(12) United States Patent
Li et al.

(10) Patent No.: US 10,314,336 B2
(45) Date of Patent: Jun. 11, 2019

(54) ATOMIZER AND ELECTRONIC CIGARETTE HAVING SAME

(71) Applicant: Shenzhen First Union Technology Co., Ltd., Shenzhen, Guangdong Province (CN)

(72) Inventors: Yonghai Li, Shenzhen (CN); Zhongli Xu, Shenzhen (CN); Shuyun Hu, Shenzhen (CN); Hongyong Luo, Shenzhen (CN)

(73) Assignee: SHENZHEN FIRST UNION TECHNOLOGY CO., LTD., Shenzhen, Guangdong Province (CN)

( * ) Notice: Subject to any disclaimer, the term of this patent is extended or adjusted under 35 U.S.C. 154(b) by 357 days.

(21) Appl. No.: 15/084,464

(22) Filed: Mar. 29, 2016

(65) Prior Publication Data

US 2016/0206006 A1   Jul. 21, 2016

(30) Foreign Application Priority Data

Apr. 30, 2015   (CN) ..................... 2015 2 0273441 U

(51) Int. Cl.
| | |
|---|---|
| *A24F 47/00* | (2006.01) |
| *A61M 15/00* | (2006.01) |
| *A61M 11/00* | (2006.01) |
| *H05B 1/00* | (2006.01) |
| *H05B 3/00* | (2006.01) |
| *A61M 15/06* | (2006.01) |
| *A61M 11/04* | (2006.01) |
| *H05B 1/02* | (2006.01) |
| *H05B 3/03* | (2006.01) |

(52) U.S. Cl.
CPC ......... *A24F 47/008* (2013.01); *A61M 11/042* (2014.02); *A61M 15/06* (2013.01); *H05B 1/0202* (2013.01); *H05B 1/0244* (2013.01); *H05B 3/0014* (2013.01); *H05B 3/03* (2013.01); *A61M 2205/3368* (2013.01)

(58) Field of Classification Search
None
See application file for complete search history.

(56) References Cited

U.S. PATENT DOCUMENTS

| | | | |
|---|---|---|---|
| 2014/0060554 A1* | 3/2014 | Collett | H05B 3/265 131/328 |
| 2015/0059787 A1* | 3/2015 | Qiu | A24F 47/008 131/329 |
| 2017/0196273 A1* | 7/2017 | Qiu | A24F 47/008 |

FOREIGN PATENT DOCUMENTS

WO   WO-2013034039 A1 *   3/2013   .......... A61M 11/041

* cited by examiner

*Primary Examiner* — Linda L Gray
(74) *Attorney, Agent, or Firm* — Cheng-Ju Chiang

(57) ABSTRACT

An exemplary atomizer includes a housing, a liquid chamber defined in the housing, a heating part in the housing, an air passage, and two electrodes. The liquid chamber is configured for storing tobacco liquid. The heating part includes a liquid conductor and a heater. The liquid conductor is configured for absorbing the tobacco liquid from the liquid chamber. The heater is in contact with the liquid conductor. The heater is configured for heating the tobacco liquid to form aerosol. The air passage allows the aerosol to flow out of the atomizer. The two electrodes are arranged at one end of the housing, and electrically connected to two opposite ends of the heater. The atomizer further includes a temperature sensor configured for sensing a temperature of the heating part.

13 Claims, 4 Drawing Sheets

ATOMIZER AND ELECTRONIC CIGARETTE HAVING SAME

TECHNICAL FIELD

The present invention relates to electronic cigarettes, and particularly to an atomizer and an electronic cigarette using same.

BACKGROUND ART

A typical electronic cigarette includes an atomizer and a power supply. The atomizer includes a heating assembly having a heating element and a liquid conducting body. The liquid conducting body is configured for absorbing tobacco liquid. The heating element is configured for heating tobacco liquid in the liquid conducting body to form aerosol.

In a typical electronic cigarette, a temperature of the heating assembly is not detected. Therefore, it is difficult to precisely control the temperature of the heating assembly, and to keep a stable amount of aerosol generated by the electronic cigarette.

What is needed, therefore, is an atomizer and an electronic cigarette using same, which can overcome the above shortcomings.

SUMMARY

An atomizer includes a housing, a liquid chamber defined in the housing, a heating part in the housing, an air passage, and two electrodes. The liquid chamber is configured for storing tobacco liquid. The heating part includes a liquid conductor and a heater. The liquid conductor is configured for absorbing the tobacco liquid from the liquid chamber. The heater is in contact with the liquid conductor. The heater is configured for heating the tobacco liquid to form aerosol. The air passage allows the aerosol to flow out of the atomizer. The two electrodes are arranged at one end of the housing, and electrically connected to two opposite ends of the heater. The atomizer further includes a temperature sensor configured for sensing a temperature of the heating part.

BRIEF DESCRIPTION OF THE DRAWINGS

Many aspects of the present disclosure can be better understood with reference to the following drawings. The components in the drawings are not necessarily drawn to scale, the emphasis instead being placed upon clearly illustrating the principles of the present disclosure. Moreover, in the drawings, like reference numerals designate corresponding parts throughout the several views.

DETAILED DESCRIPTION

Figure 1:
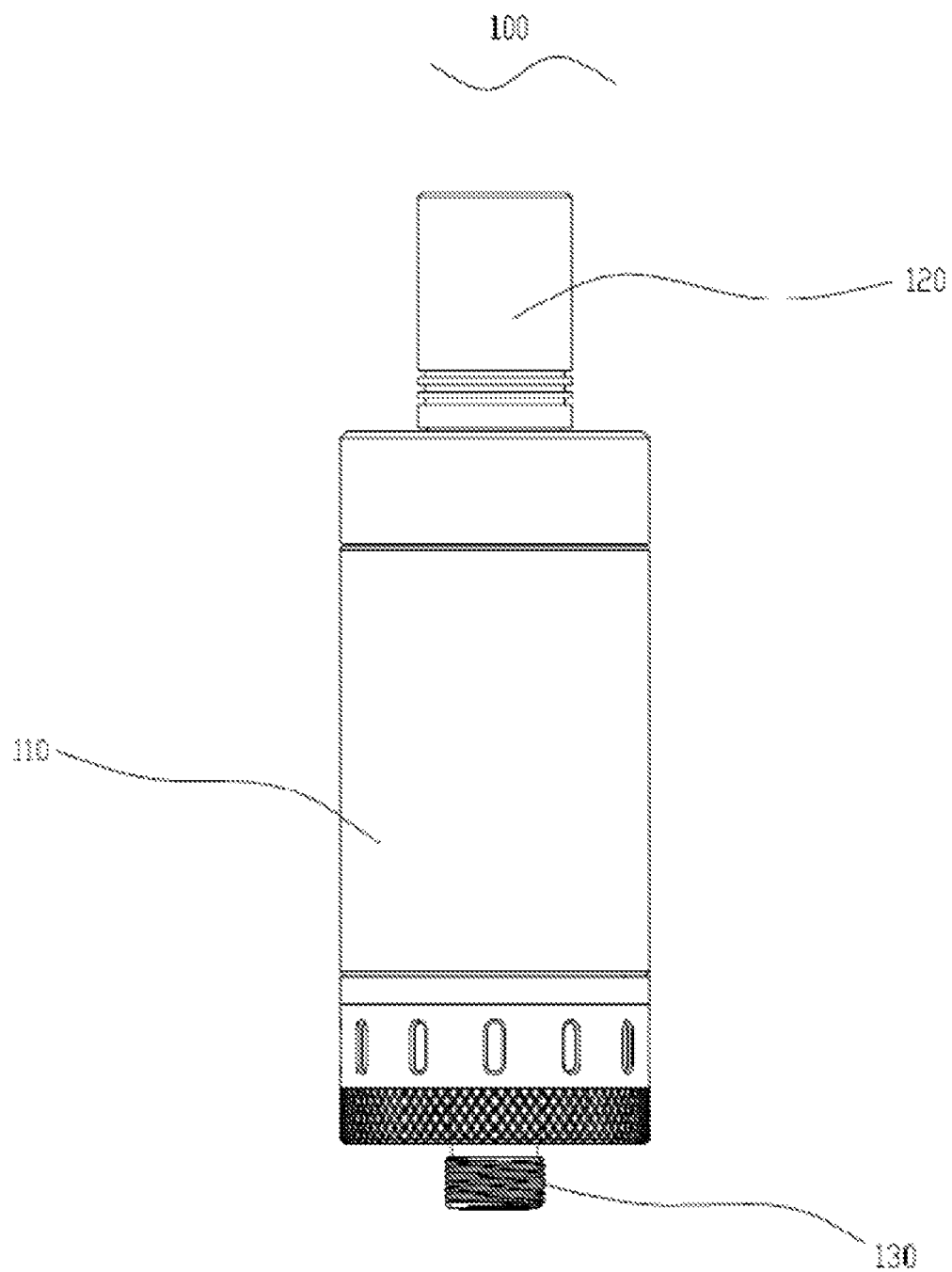
FIG. 1 is a side view of an atomizer according to a first embodiment.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts have been exaggerated to better illustrate details and features of the present disclosure.

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Several definitions that apply throughout this disclosure will now be presented.

The term "outside" refers to a region that is beyond the outermost confines of a physical object. The term "inside" indicates that at least a portion of a region is partially contained within a boundary formed by the object. The term "substantially" is defined to be essentially conforming to the particular dimension, shape or other word that substantially modifies, such that the component need not be exact. For example, substantially cylindrical means that the object resembles a cylinder, but can have one or more deviations from a true cylinder. The term "comprising," when utilized, means "including, but not necessarily limited to"; it specifically indicates open-ended inclusion or membership in the so-described combination, group, series and the like.

Figure 2:
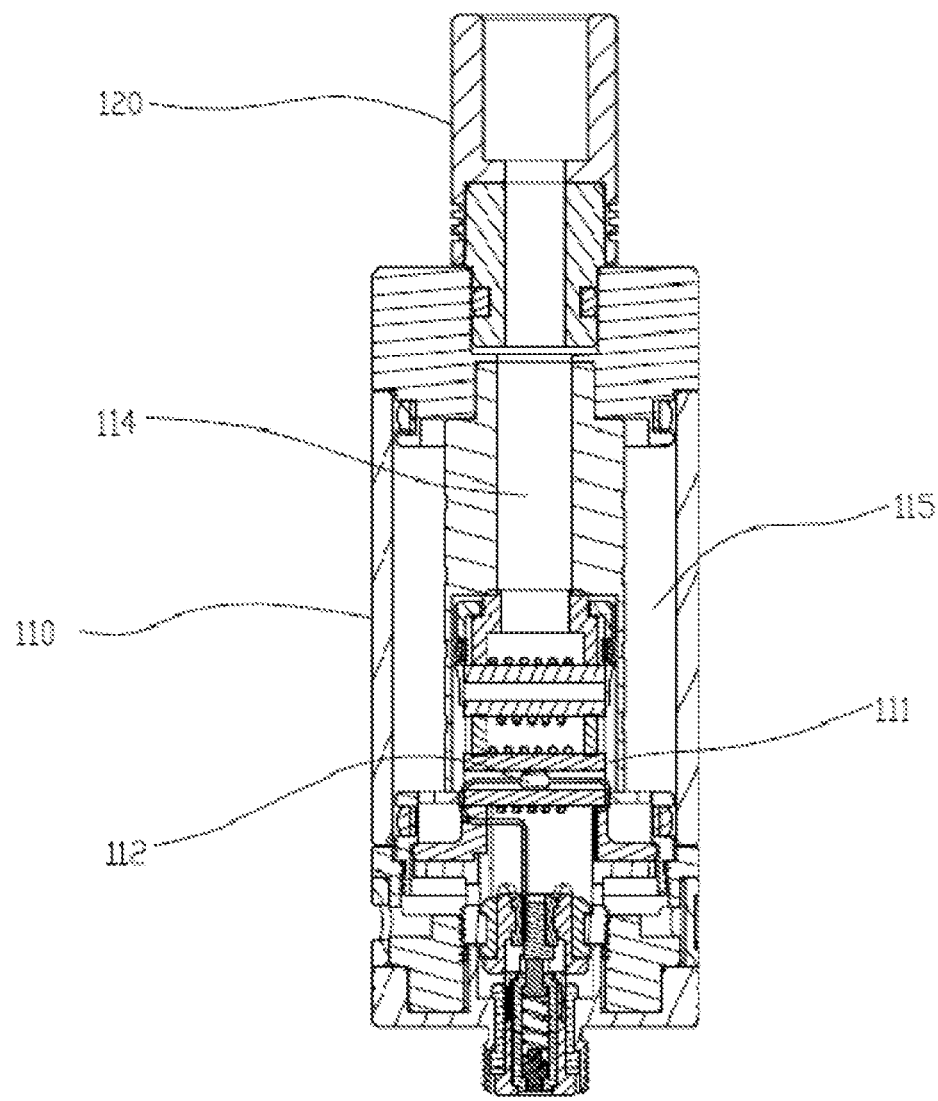
FIG. 2 is a cross-sectional view of the atomizer of FIG. 1.
Figure 3:
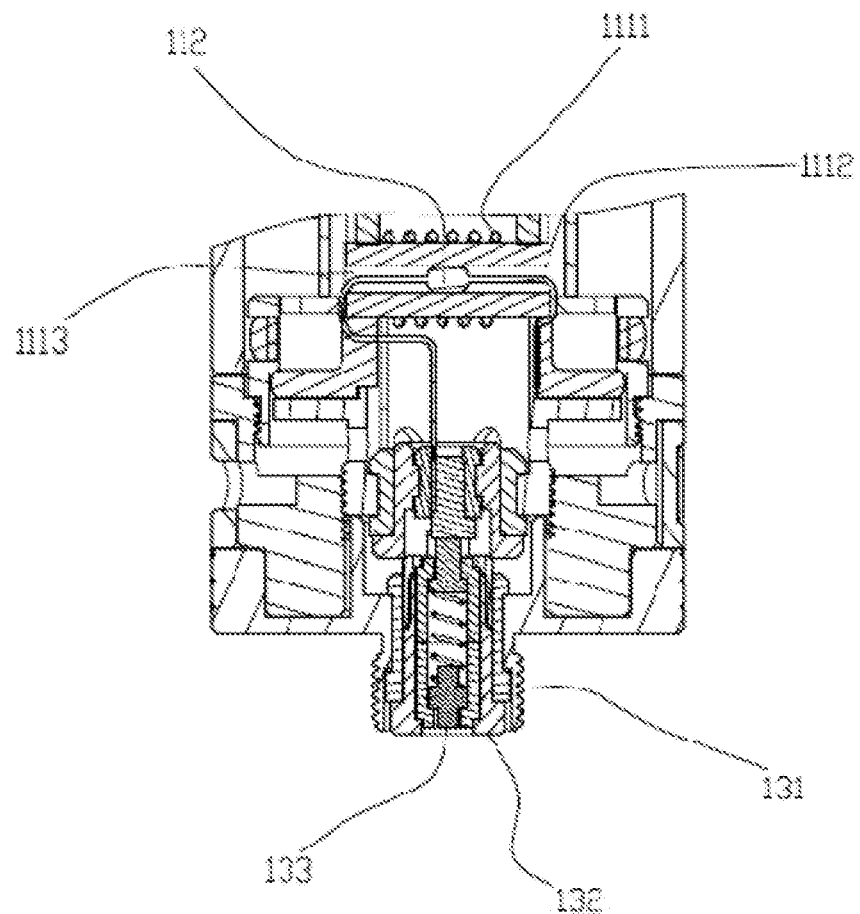
FIG. 3 is a partially enlarged view of FIG. 2.

Referring to FIGS. 1-3, an atomizer 100 is shown. The atomizer 100 includes a housing 110, a liquid chamber 115 in the housing 110, a heating part 111, and an air passage 114.

The heating part 111 includes a liquid conductor 1112 and a heater 1111. The liquid conductor 1112 is configured (i.e., structured and arranged) for absorbing tobacco liquid. The heater 1111 is in contact with the liquid conductor 1112, and configured for heating the tobacco liquid absorbed in the liquid conductor 1112 to form aerosol. A connecting part 130 including a first electrode 131 and a second electrode 132 is arranged at a first end of the housing 110, and a mouthpiece 120 is provided at an opposite second end of the housing 110. The mouthpiece 120 is in communication with the air passage 114. A temperature sensor 112 is further arranged in the housing 110. The temperature sensor 112 is configured for detecting a temperature of the heating part 111. A feedback terminal 133 is electrically connected with the temperature sensor 112. The feedback terminal 133 is provided at the first end of the housing 110 inside the connecting part 130.

In the present embodiment, the temperature sensor 112 is made of material of positive temperature coefficient (PTC). The PTC material may be nickel chromium alloy, or nickel silicon alloy. Quite usefully, the temperature sensor 112 includes a PTC thermistor.

In the present embodiment, the atomizer 110 includes two heating part 111, and each heating part 111 includes the heater 1111 and the liquid conductor 1112. The temperature sensor 112 is arranged in one of the two liquid conducting bodies 1112. The liquid conductor 1112 is made of ceramic material or glass fiber material. The liquid conductor 1112 defines a through hole 1113 extending axially. The temperature sensor 112 is located in a middle of the through hole.

Figure 4:
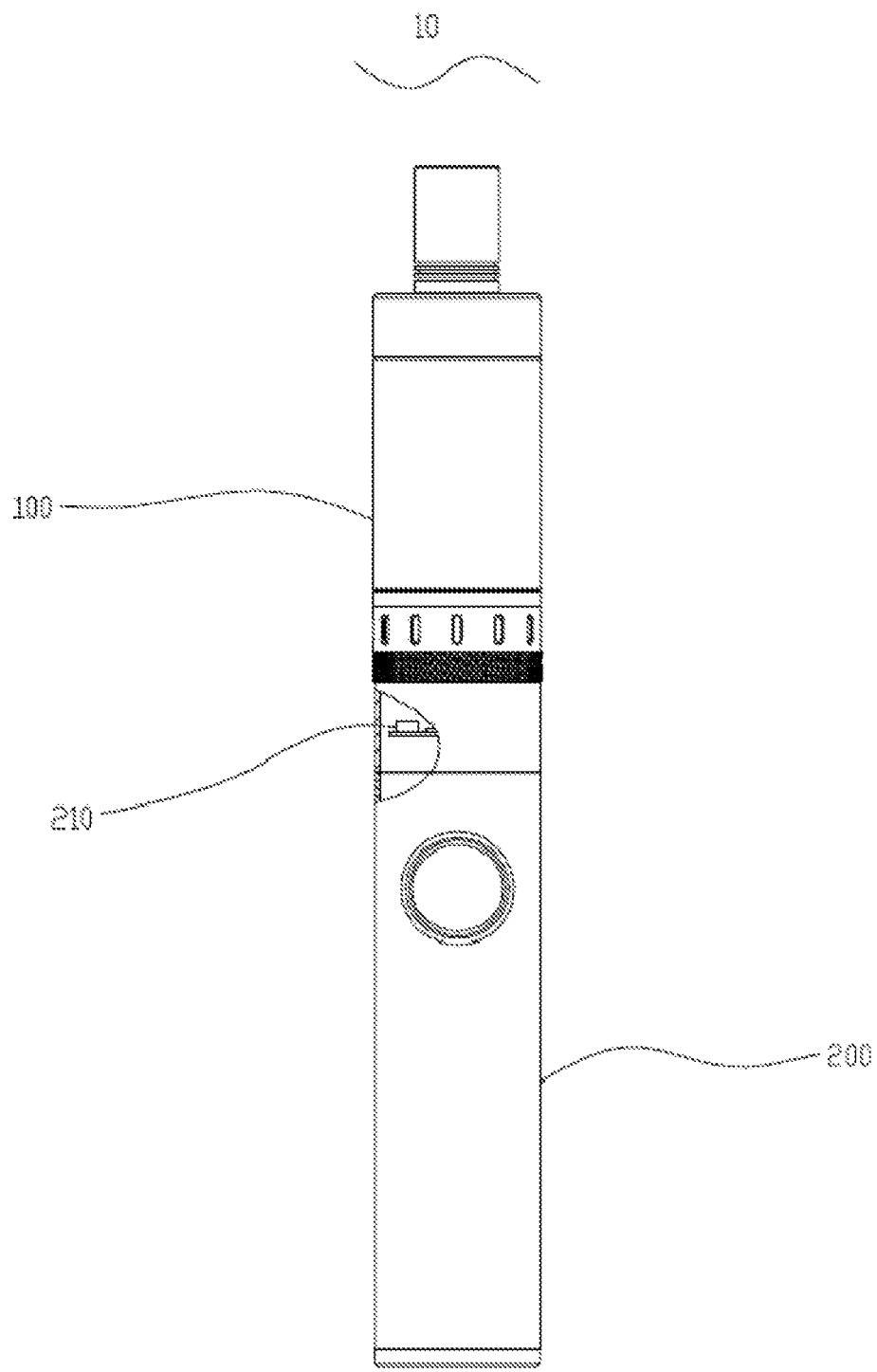
FIG. 4 is a side view of an electronic cigarette according to a second embodiment.

Referring to FIG. 4, an electronic cigarette 10 includes an atomizer 100 and a power supply 200. The atomizer 100 is detachably coupled with the power supply 200. The power supply 200 is configured for supplying the atomizer 100 power. A controller 210 is arranged in the power supply 200. The controller 210 presets a normal temperature of the liquid conductor 1112. When an actual temperature of the liquid conductor 1112 is sent back to the controller 210 via the feedback terminal 133, the controller 210 compares the actual temperature of the liquid conductor 1112 with the normal temperature, and then adjust an output wattage of the heater 1111 based on the comparing result. If the actual temperature of the liquid conductor 1112 is higher than the normal temperature, the controller 210 reduces the output wattage of the heater 1111. If the actual temperature of the liquid conductor 1112 is lower than the normal temperature, the controller 210 increases the output wattage of the heater 1111. Accordingly, a predetermined temperature of the liquid conductor 1112 is maintained, and a required amount of aerosol generated by the electronic cigarette 10 is achieved. It is to be understood that, by adjusting the predetermined normal temperature of the liquid conductor 1112, an amount of aerosol formed by the electronic cigarette 10 may be changed.

It is understood that the above-described embodiments are intended to illustrate rather than limit the disclosure. Variations may be made to the embodiments and methods without departing from the spirit of the disclosure. Accordingly, it is appropriate that the appended claims be construed broadly and in a manner consistent with the scope of the disclosure.

What is claimed is:

1. An atomizer, comprising:
   a housing;
   a liquid chamber defined in the housing, the liquid chamber being configured for storing tobacco liquid;
   a heating part in the housing, the heating part including a liquid conductor and a heater, the liquid conductor being configured for absorbing the tobacco liquid from the liquid chamber, the heater being in contact with the liquid conductor, the heater being configured for heating the tobacco liquid to form aerosol;
   an air passage allowing the aerosol to flow out of the atomizer; and
   two electrodes arranged at one end of the housing, the two electrodes being electrically connected to two opposite ends of the heater;
   wherein the atomizer further comprises a temperature sensor configured for sensing a temperature of the heating part, the temperature sensor is disposed inside the liquid conductor.

2. The atomizer in accordance with claim 1, wherein the temperature sensor is made of positive temperature coefficient (PTC) material.

3. The atomizer in accordance with claim 2, wherein the temperature sensor comprises a positive temperature coefficient (PTC) thermistor.

4. The atomizer in accordance with claim 1, wherein the liquid conductor is made of ceramic material or glass fiber material.

5. The atomizer in accordance with claim 1, wherein the liquid conductor defines a through hole extending axially, and the temperature sensor is arranged in a middle of the through hole.

6. The atomizer in accordance with claim 1, further comprising an additional heating part in the housing, wherein the additional heating part comprises a liquid conductor and a heater, and the heater is in contact with the liquid conductor.

7. The atomizer in accordance with claim 1, further comprising a mouthpiece at the other end of the housing, wherein the mouthpiece is in communication with an air pipe disposed in the atomizer for the formed aerosol to pass therethrough.

8. The atomizer in accordance with claim 1, further comprising a feedback terminal electrically connected with the temperature sensor.

9. An electronic cigarette, comprising:
   an atomizer according to claim 1; and
   a power supply configured for feeding the atomizer power, wherein the power supply comprises a controller, and the controller is configured for adjusting an output wattage of the heater based on the temperature of the heating part.

10. The electronic cigarette in accordance with claim 9, wherein the temperature sensor is made of positive temperature coefficient (PTC) material.

11. The electronic cigarette in accordance with claim 10, wherein the temperature sensor comprises a positive temperature coefficient (PTC) thermistor.

12. The electronic cigarette in accordance with claim 9, wherein the liquid conductor is made of ceramic material or glass fiber material, and the temperature sensor is arranged in the liquid conductor.

13. The electronic cigarette in accordance with claim 12, wherein the liquid conductor defines a through hole extending axially, and the temperature sensor is arranged in a middle of the through hole.

* * * * *